United States Patent
Andrade De Freitas et al.

(10) Patent No.: US 11,077,060 B2
(45) Date of Patent: Aug. 3, 2021

(54) CHITIN-GLUCAN COMPLEX, ITS PREPARATION, AND USES

(71) Applicants: Maria Filomena Andrade De Freitas, Pinhal Novo (PT); Fernando Miguel Da Silva Cruz, Cascais (PT); Maria D'Ascensão Carvalho Fernandes de Miranda Reis, Lisbon (PT); Inês Da Silva Farinha, Almada (PT)

(72) Inventors: Maria Filomena Andrade De Freitas, Pinhal Novo (PT); Fernando Miguel Da Silva Cruz, Cascais (PT); Maria D'Ascensão Carvalho Fernandes de Miranda Reis, Lisbon (PT); Inês Da Silva Farinha, Almada (PT)

(73) Assignee: PHARMA73, S. A., Borba (PT)

( * ) Notice: Subject to any disclaimer, the term of this patent is extended or adjusted under 35 U.S.C. 154(b) by 0 days.

(21) Appl. No.: 15/312,546

(22) PCT Filed: May 19, 2015

(86) PCT No.: PCT/IB2015/000708
§ 371 (c)(1),
(2) Date: Nov. 18, 2016

(87) PCT Pub. No.: WO2015/177622
PCT Pub. Date: Nov. 26, 2015

(65) Prior Publication Data
US 2017/0079917 A1   Mar. 23, 2017

Related U.S. Application Data

(60) Provisional application No. 62/001,306, filed on May 21, 2014.

(51) Int. Cl.
| | |
|---|---|
| *A61K 8/99* | (2017.01) |
| *A61Q 19/00* | (2006.01) |
| *A61K 9/14* | (2006.01) |
| *A61K 9/20* | (2006.01) |
| *A61K 9/48* | (2006.01) |
| *A61K 8/73* | (2006.01) |
| *A61K 8/02* | (2006.01) |
| *A61K 9/00* | (2006.01) |
| *A61K 8/9728* | (2017.01) |
| *A61K 31/715* | (2006.01) |
| *A61K 31/722* | (2006.01) |

(52) U.S. Cl.
CPC ............ *A61K 9/146* (2013.01); *A61K 8/022* (2013.01); *A61K 8/73* (2013.01); *A61K 8/736* (2013.01); *A61K 8/9728* (2017.08); *A61K 8/99* (2013.01); *A61K 9/0075* (2013.01); *A61K 9/205* (2013.01); *A61K 9/4866* (2013.01); *A61K 31/715* (2013.01); *A61K 31/722* (2013.01); *A61Q 19/00* (2013.01); *A61K 2800/10* (2013.01); *A61K 2800/41* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 2,118,370 | A | 5/1938 | Alexander Wessblad |
| 4,992,540 | A | 2/1991 | Jamas et al. |
| 5,169,638 | A | 12/1992 | Dennis et al. |
| 5,654,007 | A | 8/1997 | Johnson et al. |
| 6,210,686 | B1 | 4/2001 | Bell et al. |
| 8,614,070 | B2 | 12/2013 | Carvalho Fernandes De Miranda Reis et al. |
| 8,679,796 | B2 | 3/2014 | Carvalho Fernandes De Miranda Reis et al. |
| 9,861,700 | B2 * | 1/2018 | Andrade De Freitas ............ A23L 29/271 |
| 2005/0002963 | A1 * | 1/2005 | Beckett .............. A61K 47/6949 424/195.15 |
| 2010/0003292 | A1 * | 1/2010 | Gautier .................... A61K 8/73 424/401 |
| 2010/0221382 | A1 | 9/2010 | Teissedre et al. |
| 2011/0159288 | A1 | 6/2011 | Carvalho Fernandes De Miranda Reis et al. |
| 2013/0251806 | A1 * | 9/2013 | Andrade De Freitas ............ A61K 47/36 424/489 |

FOREIGN PATENT DOCUMENTS

| | | | |
|---|---|---|---|
| EP | 2221358 A1 | | 8/2010 |
| EP | 2321419 A2 * | | 5/2011 |
| GB | 2259709 A | | 3/1993 |
| WO | WO 2003/068824 A1 | | 8/2003 |
| WO | WO 2004/092391 | | 10/2004 |
| WO | WO 2006/121803 A1 | | 11/2006 |
| WO | WO 2010/013174 A2 * | | 2/2010 |
| WO | WO 2013/140222 A1 | | 9/2013 |

OTHER PUBLICATIONS

International Search Report in connection with PCT International Application No. PCT/IB2015/000708.

(Continued)

*Primary Examiner* — Celeste A Roney
(74) *Attorney, Agent, or Firm* — Gary J. Gershik

(57) ABSTRACT

A biocomposite powder comprising 20-95% (w/w) chitin-glucan complex (CGC), and up to 50% (w/w) mannose-containing polysaccharides, wherein the biocomposite powder has a bulk density of 0.5 to 1.0 g/cm$^3$, and wherein greater than 60% (w/w) of the particles of the biocomposite powder have a size below 212 μm.

20 Claims, 3 Drawing Sheets

(56) References Cited

OTHER PUBLICATIONS

Written Opinion of the International Searching Authority in connection with PCT International Application No. PCT/IB2015/000708.
Jul. 1, 2013 International Search Report issued in connection with PCT International Application No. PCT/IB2013/000403.
Jul. 1, 2013 Written Opinion of the International Searching Authority issued in connection with PCT International Application No. PCT/IB2013/000403.
Jun. 25, 2013 Office Action issued in connection with Canadian Patent Application No. 2,809,279.
Aug. 22, 2013 Amendment in Response to dated Jun. 25, 2013 Office Action in connection with Canadian Patent Application No. 2,809,279.
Sep. 20, 2013 Office Action issued in connection with Canadian Patent Application No. 2,809,279.
Oct. 21, 2013 Amendment in Response to dated Sep. 20, 2013 Office Action issued in connection with Canadian Patent Application No. 2,809,279.
Nov. 13, 2013 Voluntary Amendment in connection with Canadian Patent Application No. 2,809,279.
Nov. 21, 2013 Notice of Allowance in connection with Canadian Patent Application No. 2,809,279.
Jan. 7, 2015 Office Action issued in connection with U.S. Appl. No. 13/837,828.
May 4, 2015 Amendment in Response to dated Jan. 7, 2015 Office Action in connection with U.S. Appl. No. 13/837,828.
Sep. 21, 2015 Office Action issued in connection with U.S. Appl. No. 13/837,828.
Mar. 21, 2016 Response to dated Sep. 21, 2015 Office Action issued in connection with U.S. Appl. No. 13/837,828.
Jun. 21, 2016 Supplemental Amendment in Response to dated Sep. 21, 2015 Office Action issued in connection with U.S. Appl. No. 13/837,828.
Jul. 15, 2016 Office Action issued in connection with U.S. Appl. No. 13/837,828.
Christophe Roca, et al.; "Production of yeast chitin-glucan complex from biodiesel industry byproduct"; Process Biochemistry; 2012; pp. 1670-1675; 47; Elsevier.
Chagas B., et al.; "Production of chitin-glucan complex (CGC) from biodiesel industry byproduct"; Journal of Biotechnology, vol. 150, Nov. 1, 2010, pp. 381-382.
Cynthia M. Gallaher, et al.; "Cholesterol Reduction by Glucomannan and Chitosan Is Mediated by Changes in Cholesterol Absorption and Bile Acid and Fat Excretion in Rats"; The Journal of Nutrition; Nov. 1, 2000, vol. 130, No. 11; pp. 2753-2759.
Albertina C. Zacour, et al.; "Effect of Dietary Chitin on Cholesterol Absorption and Metabolism in Rats"; Journal of Nutritional Science and Vitaminology; 1992; vol. 38; pp. 609-613.

Musarrat H. Mohammed, et al., "Extraction of chitin from prawn shells and conversion to low molecular mass chitosan"; Food Hydrocolloids; 2013; vol. 31; pp. 166-171.
Sigma-Aldrich (http://www.sigmaaldrich.com/catalog/product/sigma/89862?lang=en&region=US); Accessed Nov. 14, 2016.
Bays et al.. Chitin-glucan fiber effects on oxidized low-density lipoprotein: a randomized controlled trial. European journal of clinical nutrition. Jan. 1, 2013;67(1):2-7.
Communication pursuant to Article 94(3) EPC dated Oct. 2, 2015 in connection with European Patent Application No. 13721 379.9.
Response to Communication pursuant to Article 94(3) EPC filed Jan. 28, 2016 in connection with European Patent Application No. 13721 379.9.
First Office Action dated May 3, 2016 in connection with Chinese Patent Application 201380016117.2 including English language summary thereof.
Response to First Office Action filed Sep. 19, 2016 in connection with Chinese Patent Application 201380016117.2 including English language draft thereof.
Jul. 3, 2012 Office Action issued in connection with U.S. Appl. No. 13/056,902.
Jan. 3, 2013 Amendment in Response to dated Jul. 3, 2012 Office Action submitted in connection with U.S. Appl. No. 13/056,902.
Apr. 5, 2013 Final Office Action issued in connection with U.S. Appl. No. 13/056,902.
Jun. 3, 2013 Amendment in Response to dated Apr. 5, 2013 Final Office Action submitted in connection with U.S. Appl. No. 13/056,902.
Jun. 18, 2013 Advisory Action issued in connection with U.S. Appl. No. 13/056,902.
Jul. 25, 2013 Amendment in Response to dated Jun. 18, 2013 Advisory Action and dated Apr. 5, 2013 Final Office Action submitted in connection with U.S. Appl. No. 13/056,902.
Aug. 19, 2013 Notice of Allowance issued in connection with U.S. Appl. No. 13/056,902.
Celik et al., Use of Biodiesel Byproduct Crude Glycerol as the Carbon Source for Fermentation Processes by Recombinant Pichia pastoris. Ind. Eng. Res. 47:2985-2990. Published on Web Apr. 3, 2008.
Kishore D. Rane et al.; "Production of Chitosan by Fungi"; Food Biotechnology (New York), vol. 7,No. 1, 1993, pp. 11-33.
Ivshin et al., "Methods for Isolation of Chitin-Glucan Complexes from Higher Fungi Native Biomass", Polymer Sciences, vol. 49, No. 11-12,2007, pp. 305-310.
M. Beran et al. "Isolation and Some Applications of Fungal Chitin-Glucan Complex and Chitosan" 2004.
Jozef Synowiecki et al. "Production, Properties, and Some New Applications of Chitin and Its Derivatives" Critical Reviews in Food Science and Nutrition, vol. 43, No. 2, Mar. 2003, pp. 145-171.
B. Chagas et al.; "Extraction and Purification of Cell Wall Polysaccharides from Pichia Pastoris Biomass" New Biotechnology, vol. 25, Sep. 1, 2009, p. S214.
International Search Report for PCT/IB2009/053189 dated Mar. 10, 2010.
Invitrogen (Pichia Fermentation Process Guidelines. 2002:1-11).

* cited by examiner

US 11,077,060 B2

CHITIN-GLUCAN COMPLEX, ITS PREPARATION, AND USES

CROSS-REFERENCE TO RELATED APPLICATIONS

This application is a § 371 national stage of PCT International Application No. PCT/IB2015/000708, filed May 19, 2015, claiming the benefit of U.S. Provisional Application No. 62/001,306, filed May 21, 2014, the content of each of which is hereby incorporated by reference into the application.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to, which this invention pertains.

BACKGROUND OF THE INVENTION

Pharmaceutical tablets and capsules often contain one or more excipients which act as binders, fillers, disintegrants, diluents, lubricants, preservatives, and/or antioxidants. Powdered excipients can be used to bulk up a drug formulation in order to allow for accurate dispensation of the active pharmaceutical ingredient when producing a dosage form.

Powder flow is a critical component for the manufacture of pharmaceutical tablets and capsules (Shah 2008). For example, tablets are often manufactured on a rotary multi-station tablet press by filling the tablet die with powder from a hopper based on volume. Capsules are also filled based upon powder volume. The rate of discharge (M) from a hopper for a free flowing powder can be calculated by the empirical equation $=\pi/4\rho_b\sqrt{D^5g2\tan\alpha}$, where $\rho_b$ is the bulk density of the powder, D is the opening diameter of the hopper, and $\alpha$ is the angle of the hopper walls (Holdich 2002). Thus, the rate of discharge from a hopper increases with increasing bulk density of the powder. Higher discharge rates allow for higher machine speeds and greater productivity.

New pharmaceutical excipients having high bulk densities allowing for increased machine speeds and higher productivity are needed.

BRIEF DESCRIPTION OF THE INVENTION

The invention provides a biocomposite powder comprising 20-95% (w/w) chitin-glucan complex (CGC), and up to 50% (w/w) mannose-containing polysaccharides, wherein the biocomposite powder has a bulk density of 0.5 to 1.0 g/cm³, and wherein greater than 60% (w/w) of the particles of the biocomposite powder have a size below 212 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm³, and wherein the particles of the biocomposite powder have a size greater than 212 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm³, and wherein the particles of the biocomposite powder have a size of 160 to 212 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm³, and wherein the particles of the biocomposite powder have a size of 100 to 160 μm.

The invention provides a biocomposite powder, comprising a chitin-glucan complex (CGC), and up to 50% (w/w) mannose-containing polysaccharides, wherein the biocomposite powder has a bulk density of 0.5 to 1.0 g/cm³, and wherein the particles of the biocomposite powder have a size of 75 to 100 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm³, and wherein the particles of the biocomposite powder have a size of 40 to 75 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm³, and wherein the particles of the biocomposite powder have a size of less than 40 μm.

The invention provides a biocomposite powder comprising a mixture of a biocomposite powder of the invention with at least one different biocomposite powder comprising a chitin-glucan complex, wherein the at least one different biocomposite powder has a bulk density of 0.5 to 1.0 g/cm³, and a particle size of less than 40 μm, 40 to 75 μm, 75-100 μm, 100-160 μm, 160-212 μm, greater than 212 μm, or a combination thereof.

The invention also provides a pharmaceutical product comprising the biocomposite powder of the invention and an active pharmaceutical ingredient.

The invention also provides a cosmetic product comprising the biocomposite powder of the invention and one or more additional ingredients.

The invention also provides a process for making the biocomposite powder of the invention, comprising
a) drying a wet biocomposite form a dried biocomposite; and
b) milling the dried biocomposite to produce the biocomposite powder.

The invention also provides a product produced by a process of the invention.

DETAILED DESCRIPTION OF THE INVENTION

Figure 1:
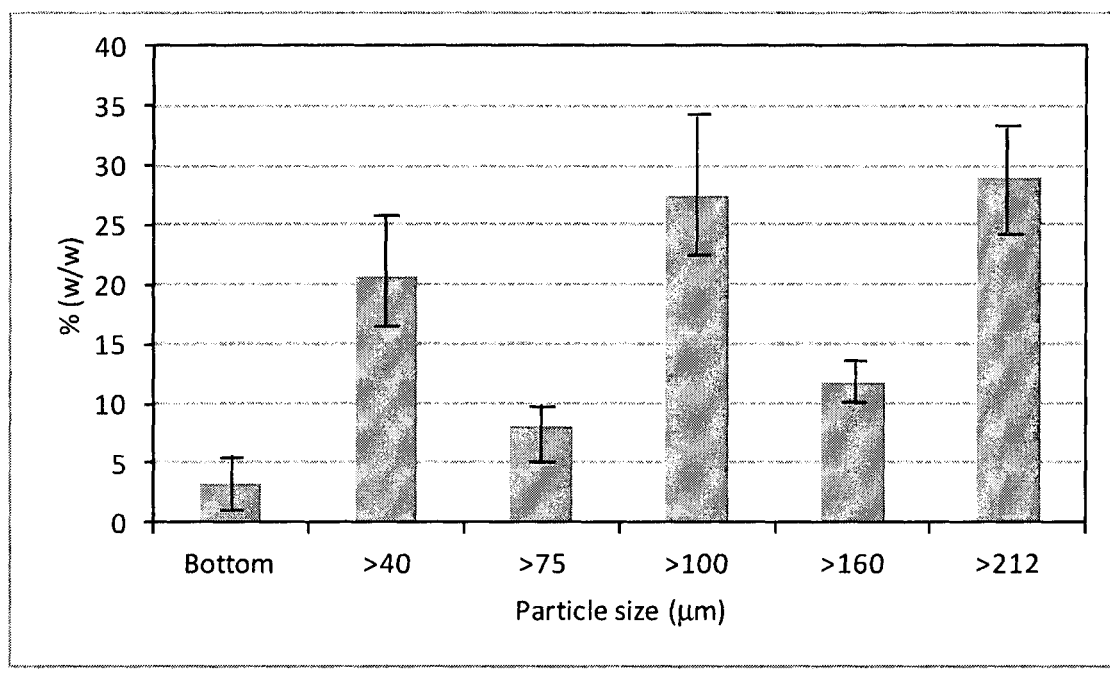
FIG. 1: Granulometric histogram of fractions of Example 2.

The invention provides a biocomposite powder comprising 20-95% (w/w) chitin-glucan complex (CGC), and up to 50% (w/w) mannose-containing polysaccharides, wherein the biocomposite powder has a bulk density of 0.5 to 1.0 g/cm³, and wherein greater than 60% (w/w) of the particles of the biocomposite powder have a size below 212 μm.

In some embodiments, 65% (w/w) of the particles of the biocomposite powder have a size below 212 μm.

In some embodiments, 70%, 75%, 80%, 85%, 90%, 95%, or 100% (w/w) of the particles of the biocomposite powder have a size below 212 μm.

In some embodiments, no less than 45% (w/w) of the particles have a size of 75 to 100 μm.

In some embodiments, no less than 25% (w/w) of the particles have a size of 100 to 160 μm.

In some embodiments, no more than 15% (w/w) of the particles have a size of 160 to 212 μm.

In some embodiments, no more than 20% of the particles have a size of less than 75 μm.

In some embodiments, no more than 20% (w/w) of the particles have a size below 75 μm, no less than 45% (w/w) of the particles have a size from 75 μm to 100 μm, no less than 25% (w/w) of the particles have a size from 100 μm to 160 μm, and no more than 15% (w/w) of the particles have a size from 160 μm to 212 μm.

In some embodiments, 20-35% (w/w) of the particles have a size above 212 μm.

In some embodiments, 5-15% (w/w) of the particles have a size from 160 to 212 μm.

In some embodiments, 20-35% (w/w) of the particles have a size from 100 to 160 μm.

In some embodiments, 5-15% (w/w) of the particles have a size from 75 to 100 μm.

In some embodiments, 10-30% (w/w) of the particles have a size from 40 to 75 μm.

In some embodiments, 0.5-10% (w/w) of the particles have a size less than 40 μm.

In some embodiments, no more than 70% (w/w) of the particles have a size from 40 μm to 75 μm and no more than 30% (w/w) of the particles have a size less than 40 μm.

In some embodiments, no more than 90% (w/w) of the particles have a size from 40 μm to 75 μm and no more than 10% (w/w) of the particles have a size less than 40 μm.

In some embodiments, 70-90% (w/w) of the particles have a size from 40 μm to 75 μm and 10-30% (w/w) of the particles have a size less than 40 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm$^3$, and wherein the particles of the biocomposite powder have a size greater than 212 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm$^3$, and wherein the particles of the biocomposite powder have a size of 160 to 212 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm$^3$, and wherein the particles of the biocomposite powder have a size of 100 to 160 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm$^3$, and wherein the particles of the biocomposite powder have a size of 75 to 100 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm$^3$, and wherein the particles of the biocomposite powder have a size of 40 to 75 μm.

The invention provides a biocomposite powder comprising a chitin-glucan complex (CGC), and up to 50% (w/w) mannose-containing polysaccharides, wherein the biocomposite powder has a bulk density of 0.5 to 1.0 g/cm$^3$, and wherein the particles of the biocomposite powder have a size of less than 40 μm.

The invention provides a biocomposite powder comprising a mixture of any one of the six above biocomposite powder with at least one different biocomposite powder comprising a chitin-glucan complex, wherein the at least one different biocomposite powder comprising a chitin-glucan complex has a bulk density of 0.5 to 1.0 g/cm$^3$, and a particle size of less than 40 μm, 40 to 75 μm, 75-100 μm, 100-160 μm, 160-212 μm, greater than 212 μm, or a combination thereof.

In some embodiments, the mixture is a mixture of two, three, four, five, or six biocomposite powders of the invention.

In some embodiments, wherein the bulk density of the biocomposite powder is 0.8-1.0 g/cm$^3$.

In some embodiments, the bulk density of the biocomposite powder is 0.8-0.9 g/cm$^3$.

In some embodiments, the bulk density of the biocomposite powder is 0.80-0.85 g/cm$^3$, 0.85-0.90 g/cm$^3$, 0.90-0.95 g/cm$^3$, or 0.95-1.0 g/cm$^3$.

In some embodiments, the tapped density of the biocomposite powder is 1.0-1.1.

In some embodiments, the biocomposite powder has a Carr Index of 9-20.

In some embodiments, the biocomposite powder has a Carr Index of 10-12, 12-14, 14-16, 16-18, 18-20, 9-12, 12-15, 15-18, 17-20, 9, 10, 11, 12, 13, 14, 15, 16, 17, 18, 19, or 20.

In some embodiments, the biocomposite powder has a Carr index of 9-12.

In some embodiments, the biocomposite powder has a stability index of 0.9 to 1.1.

In some embodiments, the biocomposite powder has a stability index of 0.6, 0.7, 0.8, 0.9, 1.0, or 1.1.

In some embodiments, the biocomposite powder has a flow rate index of 0.9 to 1.4.

In some embodiments, the biocomposite powder has a flow rate index of 0.9, 1.0, 1.1, 1.2, 1.3, or 1.4.

In some embodiments, the biocomposite powder has a conditioned bulk density of 0.5 to 1.0 g/cm$^3$.

In some embodiments, the biocomposite powder has a conditioned bulk density of 0.5, 0.6, 0.7, 0.8, 0.9, or 1.0 g/cm$^3$.

In some embodiments, the biocomposite powder has a conditioned bulk density of 0.70 to 0.85 g/cm$^3$.

In some embodiments, the chitin-glucan complex and mannose-containing polysaccharides are extracted from *Komagataella pastoris*.

In some embodiments, the *Komagataella pastoris* is strain DSM 70877.

In some embodiments, the biocomposite powder comprises 1%, 5%, 10%, 15%, 20%, 25%, 30%, 35%, 40%, 45%, or 50% mannose-containing polysaccharides.

In some embodiments, the biocomposite powder comprises 1-5%, 1-10%, 1-20%, 1-30%, 1-40%, 1-50%, 5-10%, 10-15%, 10-20%, 15-20%, 15-25%, 20-25%, 20-30%, 25-30%, 25-35%, 30-35%, 30-40%, 35-40%, 35-45%, 40-45%, or 45-50% mannose-containing polysaccharides.

The invention also provides a pharmaceutical product comprising the biocomposite powder of the invention and an active pharmaceutical ingredient.

In some embodiments, the pharmaceutical product is a tablet or a capsule.

In some embodiments, the pharmaceutical product is a dry powder inhaler formulation in which the active pharmaceutical ingredient is adsorbed to the biocomposite powder or encapsulated by the biocomposite powder.

The invention also provides a cosmetic product comprising the biocomposite powder of the invention and one or more additional ingredients.

In some embodiments, the one or more additional ingredients comprises water, glycerin, a plant oil, a plant butter, an acid, a vitamin, an antioxidant, a pigment, and/or a fragrance.

The invention also provides a process for making the biocomposite powder of the invention, comprising
 a) drying a wet biocomposite to form a dried biocomposite; and
 b) milling the dried biocomposite to produce the biocomposite powder.

In some embodiments, step a) comprises drying the wet biocomposite in an aerated oven at a temperature between 40° C. and 100° C. for 6-24 hours.

In some embodiments, the oven temperature is 40° C., 45° C., 50° C., 55° C., 60° C., 65° C., 70° C., 75° C., 80° C. 85° C., 90° C., 95° C. or 100° C.

In some embodiments, the wet biocomposite is dried for 6, 8, 10, 12, 13, 14, 15, 16, 17, 18, 20 or 24 hours.

In some embodiments, the wet biocomposite is dried until the water content of the biocomposite is less than 10%, less than 9%, less than 8%, less than 7%, less than 6%, or less than 5%.

In some embodiments, the wet biocomposite is dried in an aerated oven at a temperature of 70° C. for 16 hours.

In some embodiments, the wet biocomposite is dried in an aerated oven under vacuum.

In some embodiments, the dried biocomposite produced in step a) is washed with a solvent and lyophilized prior to step b).

In some embodiments, step b) comprises fragmentation of the dried biocomposite followed by sieving.

In some embodiments, the process further comprises, prior to step a), a step of forming wet biocomposite comprising
 i) contacting biomass containing the chitin-glucan complex and mannose containing polysaccharides with an alkaline aqueous solution to form a reaction mixture;
 ii) separating the reaction mixture into an alkaline insoluble fraction and an alkaline soluble fraction; and
 iii) washing the alkaline insoluble fraction one or more times with one or more solvents to form the wet biocomposite.

In some embodiments, step (i) is performed at a temperature of 60 to 70° C.

In some embodiments, the biomass comprises *Komagataella pastoris*.

In some embodiments, the *Komagataella pastoris* is strain DSM 70877.

In some embodiments, the alkaline insoluble fraction and the alkaline soluble fraction are separated by centrifugation, filtration, or sedimentation.

In some embodiments, the one or more solvents of step iii) is water, an aqueous saline solution, acetone, an alcohol, an aqueous solution of an acid, or a combination thereof.

In some embodiments, the alcohol is ethanol, methanol, propanol, or a combination thereof.

The invention also provides a product produced by a process of the invention.

Terms

As used herein, "Basic Flowability Energy" or "Basic Flow Energy" (BFE) refers to the value of Energy Test 7 carried out as described in Example 3.

As used herein, "bulk density" refers to the apparent density of a powder before settling determined according to European Pharmacopeia 2.9.15.

As used herein, "Carr Index" refers to a value calculated using the following equation:

$$\text{Carr Index} = \left(\frac{\text{tapped density} - \text{bulk density}}{\text{tapped density}}\right) \times 100$$

As used herein, "chitin-glucan complex" (CGC) means a copolymer of chitin (a polymer of N-acetylglucosamine units) covalently linked to β-1,3-glucans (polymers of glucose units).

As used herein, "conditioned bulk density" (CBD) refers to the density of a powder that remains in the test cell at the end of Energy Test 11 as described in Example 3.

CBD=Split mass/Split Volume (g/mL)

Split mass (g) and Split volume (mL) are the mass and volume of the powder, respectively, of the powder remaining in the chamber following Energy Test 11.

As used herein, "dried biocomposite" refers to a composition comprising a biocomposite having a water content which is less than 10% by weight. In some embodiments, the dried biocomposite has a water content which is less than 9, 8, 7, 6, 5, 4, 3, 2, or 1% by weight.

As used herein, "flow rate index" refers to a value calculated using the following equation:

$$\text{Flow Rate Index} = \frac{\text{Energy Test 11}}{\text{Energy Test 8}},$$

wherein Energy Test 11 and Energy Test 8 are carried out as described in Example 3.

As used herein, "stability index" refers to a value calculated using the following equation:

$$\text{Stability Index } (SI) = \frac{\text{Energy Test 7}}{\text{Energy Test 1}},$$

wherein the Energy Test 7 and Energy Test 1 are carried out as described in Example 3.

As used herein, "tapped density" refers to the apparent density of a powder after settling determined according to European Pharmacopeia 2.9.15.

As used herein, "wet biocomposite" refers to a composition comprising a biocomposite having a water content greater than 10% by weight. In some embodiments, the wet biocomposite has a water content greater than 15, 20, 25, 30, 40, 45, 50, 55, 60, 65, 70, 75, 80, 85, 90, 95, or greater than 95% by weight.

Chitin-Glucan Complex

U.S. Patent Application Publication No. US20130251806A1, incorporated by reference herein in its entirety, describes the production of a natural biocomposite powder comprising a CGC isolated from the biomass of yeast *Pichia pastoris* strain DSM 70877 (reclassified as *Komagataella pastoris* strain DSM 70877). In some embodiments, the biocomposite powder of the present invention is extracted from the biomass of *K. pastoris* strain DSM 70877. In other embodiments, the biocomposite powder of the present invention is extracted from the biomass of a different organism, e.g. *Aspergillus niger* (US 2010/0003292).

In some embodiments, the biomass is produced using a batch or a fed-batch fermentation process. In some embodiments, the biomass is produced using a continuous fermentation process.

Extraction of the Natural Biocomposite from *K. pastoris* Cell Wall

WO 2013/140222 describes procedures for obtaining *K. pastoris* biomass with a CGC content up to 15% (w/w) and above 15% (w/w), and describes procedures for modulating the chitin to glucan molar ratio of the CGC. These procedures can be used to obtain *K. pastoris* biomass suitable for production of the biocomposite powder of the present invention.

Natural biocomposite suitable for the production of the biocomposite powder of the present invention can be extracted from *K. pastoris* biomass using, for example, the procedures described in WO 2013/140222 or by the procedures described herein.

In some embodiments, the natural biocomposite is extracted from *K. pastoris* biomass by first contacting the *K. pastoris* biomass with a 0.2 to 5.0 M alkaline aqueous solution to form a biomass suspension. In some embodiments, the alkaline aqueous solution is NaOH, KOH, $Ca(OH)_2$, $Na_2CO_3$, $K_2CO_3$, $CaCO_3$, $NaHCO_3$, or $KHCO_3$. In some embodiments, the alkaline aqueous solution is a solution of NaOH or $NaHCO_3$. In some embodiments, the suspension has a biomass content between 10 and 15% (w/v).

In some embodiments, the *K. pastoris* biomass is present in a fermentation broth and the alkaline aqueous solution is added to the fermentation broth. In some embodiments the volume of the alkaline aqueous solution added to the fermentation broth is equal to the volume of the fermentation broth.

The biomass suspension can be mixed for 1-5 hours at a temperature of 60-70° C. In some embodiments, the suspension is stirred for 2 hours at a temperature of 65° C.

The reaction mixture is then cooled, optionally mixed with a phosphate buffered saline (PBS) solution, and neutralized by the addition of acid (for example HCl) to form an alkaline soluble and alkaline insoluble fraction. In some embodiments, the reaction mixture is cooled to a temperature of 30-45° C. In some embodiments, the PBS solution comprises 20.45 g/L NaCl, 0.46 g/L KCl, 10.14 g/L $Na_2HPO_4.7H_2O$, and 0.54 g/L $KH_2PO_4$, pH 7.2. The alkaline soluble fraction is then separated from the alkaline insoluble fraction. In some embodiments, the alkaline soluble fraction is separated from the alkaline insoluble fraction by centrifugation, filtration, or sedimentation.

Following separation, one or more of the following washings can be performed on the alkaline insoluble fraction:
 i. a water wash which is repeated until the pH and the conductivity of the mixture are between 5.0 and 8.0, and below 50 µS/cm, respectively;
 ii. a wash with an aqueous saline solution, such as, for example, phosphate buffered saline (PBS) comprising 20.45 g/L NaCl; 0.46 g/L KCl; 10.14 g/L $Na_2HPO_4.7H_2O$ or 6.612 g/L $K_2HPO_4$; and 0.54 g/L $KH_2PO_4$, pH 7.2, which is repeated until the pH of the mixture is between 5.0 and 8.0;
 iii. a wash with acetone, an alcohol, or an aqueous solution thereof. In an embodiment, the alcohol is ethanol, methanol, propanol, or a combination thereof. In an embodiment, the alcohol is a 70% (v/v) aqueous solution;
 iv. a wash with an aqueous solution of an acid, such as, for example, hydrochloric acid (HCl), which is repeated until the pH of the mixture is between 5.0 and 8.0.

These washings improve the removal of residual solubilized cell components such as proteins (by washing with, e.g., water and/or PBS solution and/or HCl solution), lipids (by washing with, e.g., acetone, alcohol, and/or HCl solution), and salts (by washing with, e.g., water and/or HCl solution). The appropriate choice of the type of solvent system(s), the number of washings performed and the sequence by which they are performed is used to control the biocomposite's content in proteins, lipids and ashes.

The amount of CGC, mannose-containing polysaccharides, proteins, lipids and ashes in the natural biocomposite are adjusted by controlling the conditions of the method of preparation described above.

Drying of the Natural Biocomposite

The natural biocomposite can be dried using one of, but not limited to, the following procedures. Various industrial drying equipments such as a freeze dryer, fluidized bed dryer, conical dryer, tray dryer, belt dryer, vacuum tray dryer, rotary drier, spray dryer, or microwave dryer can be used to obtain dried biocomposite.

In one embodiment of the invention, wet biocomposite is dried by lyophilization for 48 hours. The time of lyophilization depends mostly on moisture content of the starting material and is controlled so that the moisture content is below 10%, preferably below 5%.

In another embodiment of the invention, wet biocomposite is dried in an air drying oven at a temperature between 40 and 100° C., for 6-24 hours. In an embodiment, the wet biocomposite is dried at 70° C. in an aerated oven for 16 hours. In an embodiment, the wet biocomposite is dried under vacuum.

In an embodiment, the biocomposite is spray-dried at temperatures in a range of 120 and 200° C., preferably between 130 and 150° C. One benefit of the spray-drying of the biocomposite is to obtain particles with controlled and homogeneous size, with a bulk density between 0.25 and 0.95 g/cm$^3$, preferably between 0.45 and 0.75 g/cm$^3$ and presenting essentially a spherical shape, facilitating downstream processing of the obtained powder/granules.

In an embodiment, the dried biocomposite is washed with one of the wash solvents described above and then lyophilized.

Depending on the drying procedure used, the dried natural biocomposite will be obtained in forms ranging from low density/high volume foams to high density/compact pellets, which are used to modulate the physical properties.

Milling Procedure for Preparation of the Natural Biocomposite Powder

The natural biocomposite powder of the invention can be prepared by any method known in the art for the production of powders or granules, such as fluidized bed granulation, high shear granulation, spray drying or wet granulation. In an embodiment, the dried biocomposite is milled and granulated by any industrial fragmentation and disintegrating equipment used to obtain granules and known by the people skilled in the art, such as hammer, roller, knife, blade, or disks. The granulators used in this process can be low shear, like for instance fluid-bed granulator, medium shear or high shear granulators.

In some embodiments of the invention, biocomposite dried in an aerated oven at temperatures between 40 and 100° C. is milled by passing through a comminuting mill equipped with knife impact rotor and a sieve ranging from 0.25 mm to 10 mm in the output, preferably a sieve ranging from 0.25 to 1.0 mm in the output. In some embodiments, the material obtained is processed a second time in the same equipment with a sieve ranging from 0.25 mm to 5 mm, preferably a sieve ranging from 0.25 mm to 0.5 mm. In some embodiments, the resulting granulate is passed through an oscillating and rotating sieve mill with a sieve ranging from 0.0125 to 2.5 mm.

In some embodiments, dried biocomposite is micronized by passing through a mechanical impact mill (e.g. Fitzmill® Communitor, Fitzpatrick) equipped with a 5-15 mm sieve aperture. In some embodiments, the sieve has a 9 mm square aperture. In some embodiments, the material obtained is processed through the mill a second time but with a sieve having an aperture smaller than the aperture of the sieve used in the first pass. In some embodiments, the sieve used in the second pass has a 2.3 mm square aperture.

In some embodiments, the dried natural biocomposite is milled by passing through a Cone Mill, equipped with a conical or V rotor, and a sieve ranging from 0.25 mm to 10 mm in the output, preferably a sieve ranging from 0.25 to 1.0 mm in the output. The rotor speeds used can range from 500 rpm to 5000 rpm.

In some embodiments, the natural biocomposite is milled by passing through a Ball Mill. The rotor speeds used can range from 500 rpm to 1500 rpm.

In some embodiments, the natural biocomposite can be milled by passing through a Multi Mill. The rotor speeds used can range from 500 rpm to 5000 rpm.

In some embodiments, the natural biocomposite is dried by freeze drying or by spray drying or fluidized bed drying or by conical dryer, and is passed through a roller compactor also known as a chilsonator, for instance the Chilsonator® IR520; once or twice, or as many times as considered sufficient, to obtain the powder of interest.

The powder obtained by any of the methods described above is calibrated by any of the calibration methods used by the person skilled in the art, such as screening on successive sieves followed by gravimetric measurements. For instance, the particles can be calibrated in an oscillating and rotating sieve mill equipped with a sieve ranging from 0.05 mm to 1.5 mm.

In some embodiments, a biocomposite powder is sieved in a tower of sieves stacked on top of one another in ascending degree of coarseness. In these embodiments, the powder is charged in the largest aperture sieve. After a vibration period, each granulometric size fraction is collected from the correspondent sieve. In some embodiments, sieves having aperture sizes of 212 µm, 160 µm, 100 µm, 75 µm, and/or 40 µm are used to separate a biocomposite powder of the invention into fractions having a size of greater than 212 µm, less than 212 µm, less than 160 µm, less than 100 µm, less than 75 µm, and/or less than 40 µm. In some embodiments, 212 µm, 160 µm, 100 µm, 75 µm, and 40 µm sieves are used to make fractions of particles having a size greater than 212 µm, 160-212 µm, 100-160 µm, 75-100 µm, 40-75 µm, and less than 40 µm. In some embodiments, smaller or larger aperture sieves are used to produce fractions of different sizes as desired. For example, one or more sieves having a aperture of 25, 50, 80, 90, 125, 150, 180, 200, 250 and/or larger than 250 µm can be used to prepare fractions of the desired particle size.

The natural biocomposite powder of the present invention is characterized by particles with the minimum possible porosity, preferably less than 2.5%, which is controlled by adjusting the parameters of the drying process, such as drying speed, time and temperature. The particles shape may be spherical or cylindrical or even laminated, depending on the combination of procedures performed previously, but the final shape will preferably be spherical.

Following European Pharmacopeia 2.9.15 (Apparent volume), the apparent bulk density of the obtained particles is in the range 0.5-1.0 g/cm$^3$. In some embodiments, packed density of the biocomposite powder obtained is 0.4 to 1.7 g/cm$^3$. In some embodiments, the packed density is 1.0 to 1.5 g/cm$^3$. In some embodiments, the packed density of the biocomposite powder is 0.8, 0.9, 1.0, 1.1, 1.2, 1.3, 1.4, or 1.5 g/cm$^3$.

Uses of the Biocomposite Powder of the Invention

The biocomposite powder of the invention can be used in the production of pharmaceutical, cosmetic, and/or food products.

For example, the biocomposite powder of the invention can be used as an excipient (e.g. as a filler, binder, and/or controlled release matrix) in the production of tablet or capsule pharmaceutical dosage forms. As another example, the biocomposite powder of the invention can be used as a suspending or thickening agent for oral suspensions. As another example, the biocomposite powder of the invention can be used as excipient for dry powder inhaler formulations obtained by spray drying of a suspension of CGC with adsorbed or encapsulated drug substance.

As another example, the biocomposite powder of the invention can be used as a thickener or emulsion stabilizer in lotions and creams. As another example, the biocomposite powder of the invention can be used as a thickener and/or stabilizer in food products.

For the foregoing embodiments, each embodiment disclosed herein is contemplated as being applicable to each of the other disclosed embodiments.

By any range disclosed herein, it is meant that all tenth and integer unit amounts within the range are specifically disclosed as part of the invention. Thus, for example, 0.5 to 1.0 g/cm$^3$ means that 1.0, 1.1, 1.2, 1.3, 1.4, and 1.5 g/cm$^3$ are embodiments within the scope of the invention.

This invention will be better understood by reference to the Experimental Details which follow, but those skilled in the art will readily appreciate that the specific experiments detailed are only illustrative of the invention as defined in the claims which follow thereafter.

Example 1

Production of a High Bulk Density Biocomposite

CGC was extracted from *Komagataella pastoris* biomass grown on glycerol in a fed-batch mode, as described in WO 2013/140222. The extraction procedure involved subjecting the biomass to alkaline conditions (NaOH 1M) at 65° C., for 2 h. Afterwards, the alkaline insoluble material (AIM) was separated from the alkaline soluble fraction. The AIM was washed with PBS solution (pH 7.2), water and methanol. Finally, the polymer was dried at 40° C. for 24 h. The CGC thus obtained had a chitin-glucan molar ratio between 26.8:73.2 and 38.2:61.8. The polymer also had a mannose content of 10.50±1.11 wt %, a protein content of 4.14±0.05 wt %, and a total inorganic salts content of 44.21±5.85 wt %.

Example 2

Sub-Fractionation of the Biocomposite of Example 1

The biocomposite of Example 1 processed two times using a mechanical impact mill (Fitzmill® Comminutor, Fitzpatrick). The impact mill was equipped with a sieve having a 9 mm square aperture in the first pass and a 2.34 mm sieve in the second pass. The powder was collected and sieved using a tower of 212 μm, 160 μm, 100 μm, 75 μm, and 40 μm sieves stacked on top of one another in ascending degree of coarseness. The powder was charged in the largest aperture at the top of the tower and the tower was vibrated with an amplitude of 1.5 mm for 10 minutes each run. The powder fractions were then collected from each sieve.

The granulometric distribution of the powder was as follows.

TABLE 3

Granulometric distribution of the biocomposite powder.

| | Particle size (μm) | | | | | |
|---|---|---|---|---|---|---|
| | Bottom (<40) | >40 | >75 | >100 | >160 | >212 |
| % (w/w) | 3.32 ± 1.91 | 20.61 ± 3.94 | 8.04 ± 2.24 | 27.38 ± 5.53 | 11.73 ± 1.58 | 28.29 ± 3.71 |

The results in Table 3 are shown graphically in FIG. 1.

Bulk density, tapped density, and Carr Index values were determined for several samples of the biocomposite powder prior to sieving.

TABLE 4

Bulk Density (g/mL), Tapped Density (g/mL), and Carr Index values of samples of the biocomposite powder prior to sieving

| Parameter | Unit | Value |
|---|---|---|
| Bulk Density | (g/mL) | 0.87 ± 0.11 |
| Tapped 100x | (g/mL) | 1.00 ± 0.11 |
| Carr Index | — | 13.26 ± 3.29 |

Example 3

Rheological Characterization of the Biocomposite Powder

The biocomposite powder from Example 1 and its sub-fractions from Example 2 were analyzed to determine their physical properties using a FT4 powder rheometer (Freeman Technology, Gloucestershire, UK). The FT4 powder rheometer calculates the energy needed to make a powder flow as a twisted blade rotates and moves down and up through the powder at a defined helix angle and speed.

Overview of FT4 Experiments

Stability

A friable powder that is prone to attrition (breaking down of particles) under the stresses imposed during flow, can exhibit different flow properties at the start of the test to those at the end, due to the changes in particle size and particle shape.

Instability may occur for other reasons also and powders that are cohesive and compressible may become caked or agglomerated during flow and as a result change their flow properties during a series of tests.

Therefore, the recommended starting point when measuring a powder for the first time is the Stability (Rep) program, which runs the powder through a series of identical measurements. If the powder is stable, then the result from each measurement is similar. However, if the powder changes for any reason then a trend reflecting this change is usually observed. A stability index can be calculated from these measurements:

$$\text{Stability Index } (SI) = \frac{\text{Energy Test 7}}{\text{Energy Test 1}}$$

When SI≈1, the powder is robust and not greatly affected by being made to flow. When SI>1, the powder is affected by being made to flow. Possible causes of a SI>1 include de-aeration, agglomeration, segregation, moisture uptake, and electrostatic charge. When SI<1, the powder is also affected by being made to flow. Possible causes of a SI<1 include attrition, de-agglomeration, over blending of an additive, and coating of the vessel and blade by additive.

Understanding which factors contribute to the trend observed needs to be gained with reference to what is known about the powder. For example, if the particles are small and the powder bulk cohesive, then it is possible that the powder may become agglomerated, de-aerated or caked. However, if it is known that the powder has a wide particle size distribution, it is possible that the instability is due to segregation, rather than agglomeration.

Small changes (0.9<SI<1.1) are normal for most powders and are to be expected. It is recommended that further work be carried out to understand an unstable characteristic only if the SI is outside this range.

Variable Flow Rate Method

The rate at which powders are handled and moved thorough any given process will vary from point to point. Even the most basic transfer systems will require the powder to flow at reduced rates in some places and at high rates elsewhere.

The sensitivity of a powder to flow rate is usually an important parameter when describing its flow properties. It is common that cohesive powders are more sensitive to changes in flow rate than non-cohesive or granular materials, mainly as a result of the high air content in the cohesive materials.

The variable flow rate program begins by subjecting the powder to a standard flow rate of 100 mm/s while measuring the flow energy. For subsequent tests the flow rate is reduced and the affect on the rheology is measured. This is typically carried out at 4 flow rates (see FIG. 2).

The data obtained from the stability and variable flow rate programs are used to assign the following parameters to the powder:

Basic Flowability Energy (BFE)=Energy Test 7

$$\text{Stability Index }(SI) = \frac{\text{Energy Test 7}}{\text{Energy Test 1}}$$

$$\text{Flow Rate Index} = \frac{\text{Energy Test 11}}{\text{Energy Test 8}}$$

Results

A comparison of the Stability (friability) of particles in function of the attrition and the resistance they have to be moved (Variable Flow Rate) was made between the following powders:

CGC—initial—Biocomposite powder before sub-fractioning.

CGC Sub-fraction—212 µm—Sub-fraction containing particles above 212 µm.

CGC Sub-fraction—100 µm—Sub-fraction containing particles between 100 µm and 160 µm.

CGC Sub-fraction—75 µm—Sub-fraction containing particles between 75 µm and 100 µm.

Avicel® PH 302—High density microcrystalline cellulose marketed for the production of tablets by direct compression Prosolv® Easy Tab—Commercialized ready to use mix of powders for direct compression with 96.5% of Avicel® PH 102

The bulk density of five of these powders is shown in Table 5.

TABLE 5

Bulk Density

| Powder | Bulk Density (g/cm$^3$) |
|---|---|
| Prosolv ® Easy Tab | 0.30 |
| CGC Fraction 1- initial | 0.95 |
| CGC Sub-fraction 1 - 75 µm | 0.95 |
| CGC Sub-fraction 1 - 100 µm | 0.90 |
| Avicel ® PH 302 | 0.40 |

Figure 2:
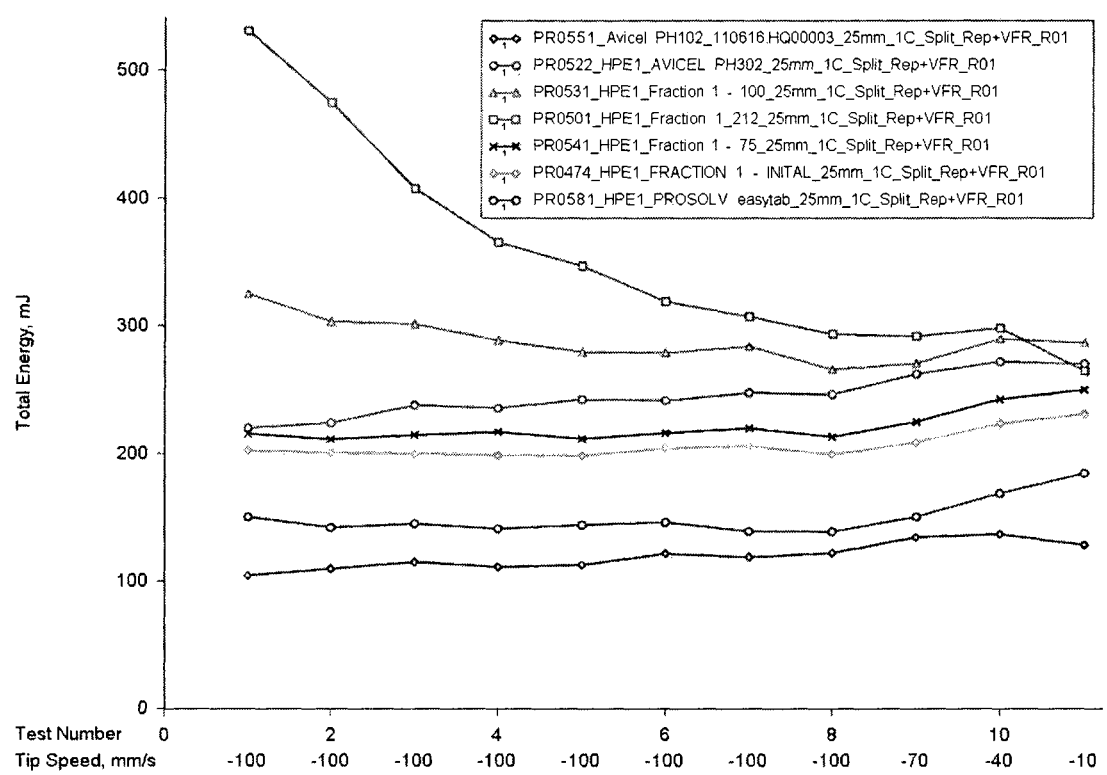
FIG. 2: FT4 plot for powders tested in Example 3.

The results of the comparison are shown in FIG. 2 and Table 6.

From the bottom to top of FIG. 2, there was an increase of the Basic Fluidization Energy (BFE). BFE is the minimal energy necessary to move the particles in each powder. These results provide information about the flowability of each powder.

High bulk density powders and/or roughness of their particles increase the BFE. In CGC powders the BFE increases with the particle size. Except for CGC Sub-fraction 1-212 µm, all lines of FIG. 2 are more or less parallel to X axis, which shows that all powders tested were stable. This also means that the powders do not produce small particles by attrition.

There was a reduction in BFE of CGC Sub-fraction—212 µm, likely because the large particles of this powder became polished after being moved.

Avicel® PH 102 had the lowest BFE due to its low density (0.26-0.31 g/cm$^3$).

Prosolv® Easy Tab had the second lowest BFE. Prosolv® Easy Tab is a commercial mixture, specially prepared and ready to use, for direct compression. It is made of 96.5% of Avicel® PH 102 plus lubricants and disintegrants which are smaller powders and are located in the surface of large particles, increasing the powder density and the attrition between large particles when moved.

The powder with the next lowest BFE was CGC—initial. It has particles of different diameters below 212 µm. Because it is a powder with high density the small particles of CGC between large particles produce a lubricating effect which lowers the BFE.

The powder with the next lowest BFE was CGC Sub-fraction 75 µm. In this case the high density of whole powder (due to large granules) superimposes to the lubricating effect of small particles (the void volume between large particles is not completed full).

The BFE of Avicel® PH 302 shows less stability because BFE increases with test number. The initial BFE is higher because the attrition of particles and increases with the test number due the erosion of the particles with the concomitant production of fine particles (high friability).

Comparing BFE profiles of CGC Sub-fraction −75 µm and Avicel® PH 302, Avicel® PH 302 has higher BFE (worse flowability) than CGC Sub-fraction−75 µm, and Avicel® PH 302 suffers more erosion (produce fine particles) during mobilization than CGC Sub-fraction −75 µm.

TABLE 6

Results

| Series Name | Material | BFE, mJ (basic flow energy) | SI (stability index) | FRI (flow rate index) | SE, mJ/g (Specific energy) | CBD, g/mL (conditioned bulk density) |
|---|---|---|---|---|---|---|
| PR0551__Avicel PH102 110616.HQ00003__25 mm_1C__Split__Rep + VFR__R01 | AVICEL ® PH102 | 118.84 | 1.137 | 1.051 | 4382.769 | 0.346 |
| PR0522__HPE1__AVICEL PH302 25 mm__1C__Split__Rep + VFR__R01 | AVICEL ® PH302 | 247.64 | 1.124 | 1.096 | 5021.092 | 0.4756 |
| PR0531__HPE1__Fraction 1 - 100 25 mm__1C__Split__Rep + VFR__R01 | CGC Sub-fraction - 100 µm | 283.744 | 0.873 | 1.077 | 4037.972 | 0.788 |
| PR0501__HPE1__Fraction 1__212 25 mm__1C__Split__Rep + VFR__R01 | CGC Sub-fraction - 212 µm | 307.010 | 0.578 | 0.9019179 | 3889.097 | 0.8252 |
| PR0541__HPE1__Fraction 1 - 75 25 mm__1C__Split__Rep + VFR__R01 | CGC Sub-fraction - 75 µm | 219.989 | 1.02 | 1.171 | 3806.317 | 0.7532 |
| PR0474__HPE1__FRACTION 1 - INITIAL 25 mm__1C__Split__Rep + VFR__R01 | CGC Sub-fraction - INITIAL | 206.10 | 1.018 | 1.159 | 346.031 | 0.844 |
| PR0581__HPE1__PROSOLV easytab 25 mm__1C__Split__Rep + VFR__R01 | PROSOLV ® Easy Tab | 139.05 | 0.9242314 | 1.329 | 3992.035 | 0.3848 |

CGC Sub-fraction −75 μm has more robust (and probably smoother) particles which increase powder flowability and reduce powder segregation (separation of fine particles from large particles).

Example 4

Compressibility of Sub-Fractions

Figure 3:
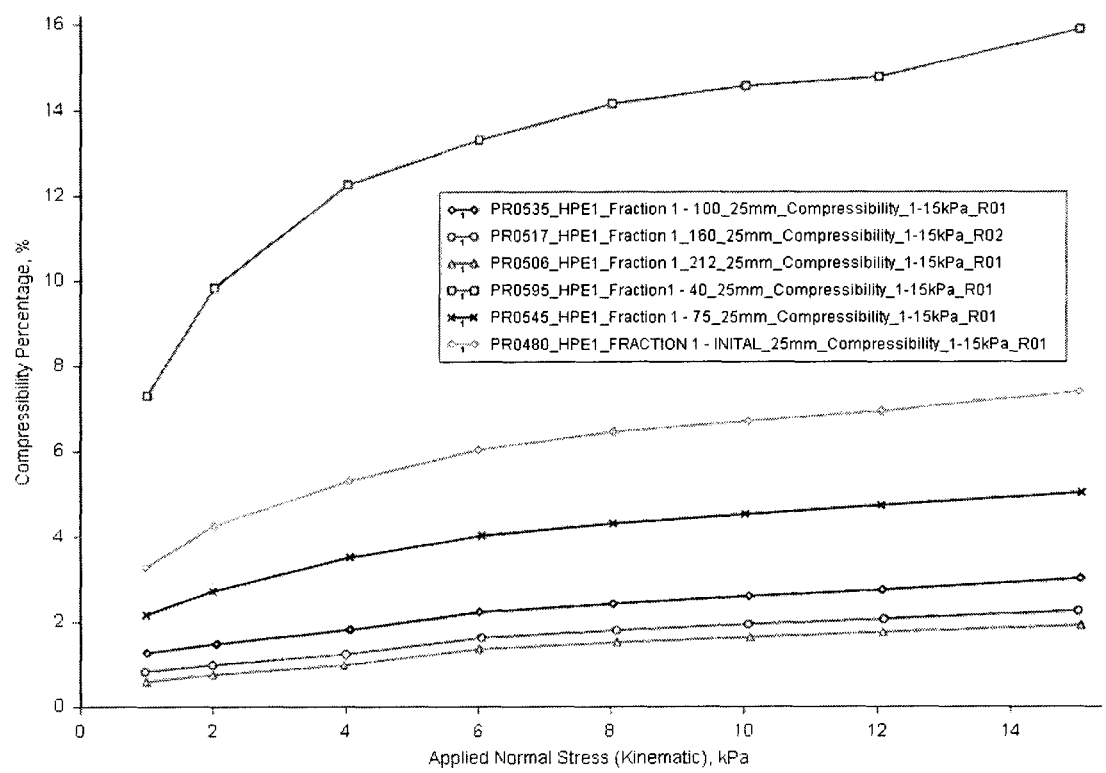
FIG. 3: Compressibility profile for powders tested in Example 4.

Compressibility trials for CGC—initial and CGC sub-fractions were performed using the FT4 powder rheometer. The results of the compressibility trials are shown in FIG. 3. FIG. 3 shows that CGC Sub-fraction—40 μm (sub-fraction of Fraction containing particles between 40 μm and 75 μm) was the most compressible of the tested sub-fractions. It is expected that CGC Sub-fraction—40 μm BFE will be higher than CGC Fraction-initial but lower than CGC Sub-fraction—75 μm.

Discussion

Examples 1-4 show that a biocomposite powder comprising a CGC and having a high bulk density can be prepared from dried CGC biocomposite. Thus, it was discovered that fractionation of the dried biocomposite allows for additional control over the bulk density of the final biocomposite powder. For example, blending of different fractions can be used to provide final CGC products having different bulk densities. The examples also show that the size profile of a final biocomposite product can be manipulated by combining different amounts of sub-fractionated biocomposite powder.

Examples 1-4 also show that the high bulk density biocomposite powders of the invention have flowability and stability properties which are comparable to or better than those of the commercial reference products.

REFERENCES

1. Shah, R. et al., "Comparative Evaluation of Flow for Pharmaceutical Powders and Granules," AAPS PharmSciTech, Vol. 9, No. 1, March 2008
2. Holdich, R. G., Chapter 10, "Powder flow and storage," *Fundamentals of Particle Technology*, 2002.
3. PCT International Publication No. WO 2013/140222, published Sep. 26, 2013 (Andrade de Freitas et al.).
4. U.S. Patent Application Publication No. 2010/0003292, published Jan. 7, 2010 (Gautier et al.)

What is claimed is:

1. A biocomposite powder comprising 20-95% (w/w) chitin-glucan complex (CGC), and 1-50% (w/w) mannose-containing polysaccharides, wherein the biocomposite powder has a bulk density of 0.8-1.0 g/cm$^3$, a tapped density of 1.0-1.1 g/cm$^3$, a Carr index of 9-20, a stability index of 0.9-1.1 and a flow rate index of 0.9-1.4, and wherein the biocomposite powder is a mixture of at least two fractions of biocomposite powder selected from:
   (a) a fraction of biocomposite powder wherein the particles of the fraction have a size greater than 212 μm;
   (b) a fraction of biocomposite powder wherein the particles of the fraction have a size of 160 to 212 μm;
   (c) a fraction of biocomposite powder wherein the particles of the fraction have a size of 100 to 160 μm;
   (d) a fraction of biocomposite powder wherein the particles of the fraction have a size of 75 to 100 μm;
   (e) a fraction of biocomposite powder wherein the particles of the fraction have a size of 40 to 75 μm; and
   (f) a fraction of biocomposite powder wherein the particles of the fraction have a size of less than 40 μm; and wherein the chitin-glucan complex and mannose-containing polysaccharides are extracted from *Komagataella pastoris*, and wherein greater than 60% (w/w) of the particles of the biocomposite powder have a size below 212 μm.

2. The biocomposite powder of claim 1, wherein:
   (a) 65% (w/w) of the particles of the biocomposite powder have a size below 212 μm;
   (b) no less than 45% (w/w) of the particles have a size of 75 to 100 μm;
   (c) no less than 25% (w/w) of the particles have a size of 100 to 160 μm;
   (d) no more than 15% (w/w) of the particles have a size of 160 to 212 μm; or
   (e) no more than 20% (w/w) of the particles have a size of less than 75 μm.

3. The biocomposite powder of claim 1, wherein no more than 20% (w/w) of the particles have a size below 75 μm, no less than 45% (w/w) of the particles have a size from 75 μm to 100 μm, no less than 25% (w/w) of the particles have a size from 100 μm to 160 μm, and no more than 15% (w/w) of the particles have a size from 160 μm to 212 μm.

4. The biocomposite powder of claim 1, wherein:
   (a) 5-15% (w/w) of the particles have a size from 160 to 212 μm;
   (b) 20-35% (w/w) of the particles have a size from 100 to 160 μm;
   (c) 5-15% (w/w) of the particles have a size from 75 to 100 μm;
   (d) 10-30% (w/w) of the particles have a size from 40 to 75 μm; or
   (e) 0.5-10% (w/w) of the particles have a size less than 40 μm.

5. The biocomposite powder of claim 1, wherein no more than 70% (w/w) of the particles have a size from 40 μm to 75 μm and no more than 30% (w/w) of the particles have a size less than 40 μm.

6. The biocomposite powder of claim 1, wherein no more than 90% (w/w) of the particles have a size from 40 μm to 75 μm and no more than 10% (w/w) of the particles have a size less than 40 μm.

7. The biocomposite powder of claim 1, wherein 70-90% (w/w) of the particles have a size from 40 μm to 75 μm and 10-30% (w/w) of the particles have a size less than 40 μm.

8. The biocomposite powder of claim 1, wherein:
   (a) the bulk density of the biocomposite powder is 0.80-0.85 g/cm$^3$, 0.85-0.90 g/cm$^3$, 0.90-0.95 g/cm$^3$, or 0.95-1.0 g/cm$^3$; or
   (b) the biocomposite powder has a conditioned bulk density of 0.70 to 0.85 g/cm$^3$.

9. The biocomposite powder of claim 8, wherein the chitin-glucan complex and mannose-containing polysaccharides are extracted from *Komagataella pastoris* strain DSM 70877.

10. A pharmaceutical product comprising the biocomposite powder of claim 1 and an active pharmaceutical ingredient.

11. The pharmaceutical product of claim 10, wherein the pharmaceutical product is a tablet or a capsule.

12. The pharmaceutical product of claim 10, wherein the pharmaceutical product is a dry powder inhaler formulation, and wherein the active pharmaceutical ingredient is adsorbed to the biocomposite powder or encapsulated by the biocomposite powder.

13. A cosmetic product comprising the biocomposite powder of claim 1 and one or more additional ingredients.

14. A process for making the biocomposite powder of claim 1, comprising
   a) drying a wet biocomposite to form a dried biocomposite; and
   b) milling and fragmentation of the dried biocomposite, followed by sieving in a tower of sieves stacked on top of one another in ascending degree of coarseness, to produce fractions of biocomposite powder of different particle sizes; and
   c) mixing the fractions to produce the biocomposite powder.

15. The process of claim 14, wherein:
   (a) step a) comprises drying the wet biocomposite in an aerated oven at a temperature between 40° C. and 100° C. for 6-24 hours;
   (b) the wet biocomposite is dried in an aerated oven at a temperature of 70° C. for 16 hours;
   (c) the wet biocomposite is dried in an aerated oven under vacuum; or
   (d) the dried biocomposite produced in step a) is washed with a solvent and lyophilized prior to step b).

16. The process of claim 14, further comprising, prior to step a), a step of forming wet biocomposite comprising
   i) contacting biomass containing the chitin-glucan complex and mannose containing polysaccharides with an alkaline aqueous solution to form suspension reaction mixture;
   ii) separating the reaction mixture into an alkaline insoluble fraction and an alkaline soluble fraction; and
   iii) washing the alkaline insoluble fraction one or more times with one or more solvents to form the wet biocomposite.

17. The process of claim 16, wherein:
   (a) step (i) is performed at a temperature between 60 to 70° C.;
   (b) the biomass comprises *Komagataella pastoris*;
   (c) the alkaline insoluble fraction and the alkaline soluble fraction are separated by centrifugation, filtration, or sedimentation; or
   (d) one or more solvents of step iii) is water, an aqueous saline solution, acetone, an alcohol, an aqueous solution of an acid, or a combination thereof.

18. The process of claim 17, wherein:
   (a) the *Komagataella pastoris* is strain DSM 70877; or
   (b) the alcohol is ethanol, methanol, propanol, or a combination thereof.

19. The cosmetic product of claim 13 wherein the one or more additional ingredients comprises water, glycerin, a plant oil, a plant butter, an acid, a vitamin, an antioxidant, a pigment, and/or a fragrance.

20. The biocomposite powder of claim 1, wherein 20-35% (w/w) of the particles of the biocomposite powder have a size above 212 µm.

* * * * *